United States Patent [19]

Nozaki

[11] 4,177,220

[45] Dec. 4, 1979

[54] 1-OCTEN-7-YNE PRODUCTION

[75] Inventor: Kenzie Nozaki, Houston, Tex.

[73] Assignee: Shell Oil Company, Houston, Tex.

[21] Appl. No.: 957,780

[22] Filed: Nov. 6, 1978

[51] Int. Cl.$^2$ .................... C07C 3/06; C07C 11/28
[52] U.S. Cl. .................................. 585/505; 585/514
[58] Field of Search ............................... 260/678

[56] References Cited

U.S. PATENT DOCUMENTS

| | | | |
|---|---|---|---|
| 3,458,562 | 7/1969 | Shier | 260/678 X |
| 3,732,328 | 5/1973 | Wright | 260/680 B |
| 3,823,199 | 7/1974 | Wright | 260/680 B |

FOREIGN PATENT DOCUMENTS 1341324  12/1973  United Kingdom ................ 260/680 B

OTHER PUBLICATIONS

Gardner et al., "Pt Metal Catalyzed Formation of Linear Octadiene", Tetrahedron Letters, No. 2, pp. 163–164 (1972).

Roffia et al., "Catalysis by Pd Salts, IV, Synthesis of 1,7-Octadiene", Journal of Organomet. Chem. 55, 405–407 (1973).

*Primary Examiner*—Delbert E. Gantz
*Assistant Examiner*—G. E. Schmitkons
*Attorney, Agent, or Firm*—Howard W. Haworth

[57] ABSTRACT

Vinyl acetylene is coupled with butadiene to selectively produce 1-octen-7-yne by reacting the vinyl acetylene with butadiene in the presence of formic acid or a salt thereof, optionally a solvent and a catalyst comprising palladium complexed with tertiary organophosphorus ligand.

9 Claims, No Drawings

1-OCTEN-7-YNE PRODUCTION

BACKGROUND OF THE INVENTION

1. Field of the Invention

The present invention relates to the production of 1-octen-7-yne by hydrocoupling butadiene and vinyl acetylene.

2. Description of the Prior Art

1-Octen-7-yne is a useful chemical intermediate. Since olefinic and acetylenic bonds have different reactivities, this subject compound is useful for synthesis of bifunctional compounds, particularly compounds having terminally distributed functional groups. Illustrative of such compounds are 1,2-epoxy-7-octyne, 6-heptynoic acid, 1,2-dibromo-7-octyne and 2-cyano-1,7-octadiene.

Hydrodimerizing butadiene with formic acid and palladium catalyst is known. Wright in U.S. Pat. No. 3,732,328 issued May 8, 1973, prepares mixtures of octadienes by reacting butadiene in the presence of a palladium compound, a polar solvent, a reducing agent and a tertiary phosphine. Wright in U.S. Pat. No. 3,832,199, issued July 9, 1974, prepares mixtures of octadiene by reacting butadienes in the presence of a palladium compound, a non-polar solvent, a reducing agent and a tertiary phosphine. Wright in British Pat. No. 1,341,324 issued Dec. 9, 1973 discloses processes similar to above. Gardner et al, Tetrahedron Letters No. 2, pp. 163–164 (1972) discloses the production of mixtures of octadiene by reacting butadiene in the presence of palladium salts, or organic base, formic acid and a phosphine. Roffia et al, Journal of Organometallic Chemistry, 55 (1973) 405–407 utilizes a phoshpine-zero valent palladium complex catalyst in benzene in the presence of formic acid to dimerize butadiene.

Hydrodimerization of vinyl acetylene is not a known process.

SUMMARY OF THE INVENTION

The process of this invention is directed to the cross hydrocoupling of vinyl acetylene and butadiene in the presence of formic acid and a catalyst comprising palladium complexed with a tertiary organo phosphorus-containing ligand. The formic acid may be present as the acid or as the salt of a base. The palladium is present in any of its possible valence states, with zero valence preferred. A suitable solvent is optionally used. The process of this invention predominately produces 1-octen-7-yne rather than, as might be expected, mixtures of 1-octen-7-yne, dimers of butadiene and dimers of vinyl acetylene.

DESCRIPTION OF THE PREFERRED EMBODIMENTS

Solvents are not essential to the process of this invention, but a good organic solvent can promote the rate of reaction by a factor of two or more.

Wright in above-cited U.S. Pat. No. 3,823,199 cites the use of non-polar solvents such as paraffinic, cycloparaffinic or aromatic which are also useful in the process of this invention. The solvent can be a paraffin or cycloparaffin containing 5 to 16 carbon atoms, such as hexane, dodecane, pentadecane, cyclohexane, methylcyclohexane and the like. Suitable solvents also include aromatic hydrocarbons such as benzene, lower alkyl substituted aromatic hydrocarbons such as toluene, m-, p- and o-xylene, halogenated aromatic hydrocarbons including chloro, bromo and iodo substituted, such as chlorobenzene and the like. Halogenated lower aliphatic compounds such as chloroform, methylene chloride, carbon tetrachloride and the like may be used, in particular chloroform is preferred.

Further useful are amine solvents such as those cited by Wright in above-noted British No. 1,341,324. A wide range of amines are useful provided that they are liquid under reaction conditions. Tertiary amines are preferred to primary and secondary amines. Suitable amine solvents include alkylamines, cycloalkylamines, arylamines and heterocyclic amines such as morpholine, pyridine, piperazine and piperidine. Examples of these classes of amines are the lower alkylamines containing 2 to 6 carbon atoms in each alkyl group such as triethylamine; mono-cyclohexylamine, and N-alkyl-cyclohexylamines containing up to 12 carbon atoms; aniline and N-alkylanilines containing up to 12 carbon atoms and N-alkylmorpholines containing up to 12 carbon atoms.

Solvents of moderate coordinating ability are quite useful and include nitriles such as lower alkyl nitriles, hydrocarbon aromatic nitriles including acetonitrile, benzonitrile and the like, amides including benzamide, acetamide, mono- and di-substituted amides where the substitutent is preferably lower alkyl. Suitable substituted amides include N-methyl acetamide, N,N dimethyl acetamide and dimethylformamide. Dialkyl sulfoxides such as dimethyl sulfoxide and sulfones such as sulfolane and alkyl-substituted sulfolane are satisfactory. By dialkyl it is meant that the sulfur and nitrogen atoms are connected to two different carbon atoms. They may be separate alkyl groups or the same, i.e., a ring alkyl group, e.g. tetramethylene sulfoxide and N-methyl pyrrolidinone. The alkyl moieties have carbon numbers ranging from 1 to about 6. Simple ethers such as the dilower alkyl ethers including dimethyl ether, diethylene, and the like function satisfactorily. Hydrocarbon aromatic ethers such as the lower alkyl phenyl ethers may be also used. In addition, the cyclic diethers such as 1,4-dioxane are also suitable solvents.

Simple lower alkyl esters of lower alkanoic acids such as ethyl acetate, methyl acetate, methyl butyrate and the like as well as cyclic diesters such as ethylene carbonate are also suitable solvents of moderate coordinating ability. Ketones, including lower aliphatic ketones such as methyl ethyl ketone and hydrocarbon aromatic ketones such as acetophenone are also satisfactory solvents. Lower mono- and di-alkanols such as isopropanol, ethylene glycol and the like may be used if desired. The preferred solvents of moderate coordinating ability include nitriles, formamides, such as dimethylformamide, dilower alkyl ethers, lower alkyl phenyl ethers, simple lower alkyl esters of lower alkanoic acids, ketones and lower alkanols.

The particularly preferred solvents utilized in this invention include benzene, dimethylformamide, chlorobenzene, anisol, N,N-dimethylacetamide, nitromethane, ethyl acetate, isopropanol, benzonitrile, chloroform, methyl ethyl ketone, acetonitrile, diethylether, acetophenone, toluene, ethylene glycol, ethylene carbonate, propylene carbonate and sulfolane. Particularly desired solvents are nitromethane, ethylene carbonate and propylene carbonate.

The preferred organic solvents will have carbon numbers ranging from 1 to about 20. Particularly desired solvents are those which give two-phase systems which allow easy product separation such as, for example, nitromethane, ethylene carbonate and propylene carbonate.

The amount of solvent added should be sufficient to dissolve the palladium compound-tertiary phosphine complex.

The formic acid is utilized as a source of hydrogen for the process. It is present in the reaction mixture as an acid or as a salt of a base. When the salt is used, it is thought that dissociation of the formic acid-base salt provides a suitable amount of formic acid necessary to provide the required hydrogen.

It is desirable that some formic acid or the salt, be present during the entire course of the reaction. When operating the process batch-wise, this can be accomplished by adding a stoichiometric amount of formic acid initially, 1 mole of formic acid for every 2 moles of butadiene, or by continuously or periodically adding additional amounts of formic acid.

A base when used must be one which can neutralize formic acid according to the reaction:

$$HCOOH + B \rightarrow HCOO^- HB^+.$$

The base may be organic or inorganic. Suitable organic bases typically have dissociation constants greater than $10^{-8}$ and include tertiary amines such as triethyl amine, tributyl amine, dimethylethyl amine, lutidine, tripropyl amine, N-methyl morpholine, isoquinoline. N-methyl-2,2,6,6-tetramethyl piperidine, 2,8-(dimethylamine) naphthalene and the like.

Suitable inorganic bases include ammonia, the hydroxide bases such as sodium hydroxide, potassium hydroxide, calcium hydroxide; ammonium hydroxide; the carbonates and bicarbonates such as sodium carbonate, sodium bicarbonate, potassium carbonate, potassium bicarbonate, calcium carbonate and the like; the weak bases such as sodium acetate, potassium acetate, ammonium carbonate, ammonium acetate and the like. When the inorganic bases are utilized, small amounts of water may be present. Preferred moles of water are at least equal to the moles of formate salts.

When organic bases are utilized, excess base may be utilized as a solvent or the amine-base salt may be used as the solvent.

The catalyst used in the process of this invention is palladium or a palladium compound complexed with a trisorgano phosphorous-containing ligand. The palladium may be in any of its possible valence states, e.g. 0, +2, etc. Suitable palladium compounds include the palladium carboxylates, particularly palladium carboxylates derived from alkanoic acids containing up to six carbon atoms such as palladium acetate (OAC), complexes such as palladium acetylacetonate (AcAc), bis-benzonitrile palladium (II) and lithium palladous chloride as well as the palladium halides, nitrates and sulfates such as palladous chloride and palladium nitrate (Pd(NO$_3$)$_2$(OH)$_2$) and palladium sulfate. Suitable reduced palladium-phosphine complexes are Pd(R$_3$P)$_2$ or Pd(R$_3$P)$_3$. The palladium is present in the reaction mixture in catalytic amounts; preferably from about 1 to about $10^{-6}$ molar and more preferably from about $10^{-1}$ to about $10^{-4}$ molar.

The palladium compounds complexed with a trisorgano phosphorous-containing ligand are typically prepared by reacting the tertiary phosphorous ligand with the appropriate palladium compound as, for example represented by the following equations:

$$2R_3P + (PhCN)_2PdCl_2 \rightarrow (R_3P)_2PdCl_2$$

$$(R_3P)_2PdCl_2 + Ag_2CO_3 \rightarrow (R_3P)_2PdCO_3$$

$$(R_3P)_2PdO_2 + SO_2 \rightarrow (R_3P)_2PdSO_4$$

$$(R_3P)_2PdO_2 + N_2O_4 \rightarrow (R_3P)_2Pd(NO_3)_2$$

where $R_3P$ is a trisorgano phosphine of the invention, or may be made in situ by adding the palladium compound and the phosphine directly to the reactor.

Any tertiary organo phosphorous ligand which can be dissolved in the reaction mixture may be used. Suitable ligands are represented by the formula:

$$(RO)_a P R_b$$

wherein R generally is hydrocarbyl and maybe the same or different and is selected from aryl, alkyl, aralkyl and alkaryl groups which contain less than about 20 carbon atoms, preferably less than about 12 carbon atoms, O is oxygen, a is an integer from 0 to 3 and b is 3-a. Suitable examples of R are phenyl, p-tolyl, o-tolyl, m-tolyl, m-chlorophenyl, p-anioly, m-anisoyl, ethyl, propyl, butyl and the like. It is also suitable for the organic radical R to contain functional groups or to satisfy more than one of the valences of the phosphorus atom, thereby forming a heterocyclic compound with the phosphorus atom. Preferably R represents aryl, alkyl, aralkyl, alkaryl or a mixture thereof having carbon numbers from 1 to about 20, preferably 1 to about 12 carbon atoms and need not be the same, e.g. $R_1R_2R_3P, (R_1O)PR_2R_3, (R_1O)(R_2O)PR_3$, etc. Preferably R is alkyl or aryl and is the same. Alternatively the formula for the ligand can be expressed as $R_c^1 R_d^2 R_e^3 P(OR^4)_f(OR^5)_g(OR^6)_h$ where c, d, e, f, g and h individually equals 0 or 1, $c+d+e+f+g+h$ equals 3 and R is as defined above. The most preferred tertiary organo phosphorus ligands have at least one R as benzyl or branched alkyl, aralkyl, alkenyl, and cycloalkyl having from 3 to about 10 carbon atoms with branching occurring at a carbon atom no more than two carbon atoms from the phosphorus or oxygen atom, This preferred R provides a steric hinderance to the catalyst complex which enhances selectivity.

Illustrative of the preferred R moiety are, for alkyl, isopropyl sec-butyl, tert-butyl, isobutyl, neopentyl, sec-pentyl, tert-pentyl, 2-methylbutyl, sec-hexyl, tert-hexyl, 2,2-dimethylpropyl; for aralkyl, alpha-methylbenzyl, alpha, alpha-dimethylbenzyl, alpha-methyl-alpha-ethyl-benzyl, phenylethyl, phenylisopropyl, phenyl-tert-butyl; for alkenyl allyl, crotyl, methallyl, 1-methyl-ethenyl, 1-methyl-2-propenyl, 2-methyl-2-propenyl, 1,1-dimethyl-2-propenyl, 1-methyl-3-butenyl and, for cycloalkyl, cyclopropyl, cyclobutyl, cyclopentyl, cyclohexyl, cycloheptyl, and the like.

Two or more of the instant phosphorus ligands may be used in the same reaction. The mole ratio of tertiary phosphorus ligand to palladium is at least 1. Preferably the mole ratio of ligand to palladium ranges from about 1:1 to about 1:20 and preferably from about 2:1 to about 5:1. The use of the tertiary phosphorus ligands of the invention provides extremely high selectivities to 1,7-octadiene.

Alternatively, the palladium compound and tertiary phosphorus ligand may be bound onto a crosslinked synthetic resin instead of being dissolved in the reaction medium. Acceptable crosslinked synthetic resins include crosslinked polystyrene, poly(alpha-alkyl) acrylates, polycarbonates, polyamides and the like. In the generic sense, the bound ligand will have the generic formula $Z-P(RO)_iR_j$ wherein R is as defined above, i is an integer from 0 to 2, j is 2-i and Z is the crosslinked synthetic resin.

The bound tertiary phosphine may have the general formula:

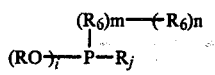

wherein R, i and j are defined previously, and $R_6$ represents the repeating unit of the synthetic resin and where m is a positive integer, n is 0 or a positive integer, m+n equals the total number of repeating units in resin and the percentage of the repeating units substituted with the tertiary phosphine is represented by the formula:

$$\frac{m}{m+n} \times 100\%.$$

The number of repeating units substituted with the tertiary phosphine is not critical. When less than 5% of the repeating units contain a phosphine substitute, large quantities of the resin must be used to form the bound catalyst. Accordingly, it is desirable to have at least 10% of the repeating units substituted with a tertiary phosphine. It is preferred, however, that from 20 to 40% of the repeating units contain a phosphine substituent. The substituent can be introduced into the resin using well-known techniques, such as those described by Smith et al in the Journal of the American Chemical Society, 97 (7) 1749 (1975) and by Pittman et al in Ann. N.Y. Academy of Sciences, 239, 76 (1974). In accordance with those techniques, the palladium compound is complexed with the phosphorus-substituted resin by admixing in a solvent for palladium acetate.

The catalyst may be pretreated to enhance reactivity by contacting it with a reducing agent at a temperature of from about 20° to about 90° C. for from about 0.1 to about 5 hours. The reducing agent may be gaseous, solid or liquid. Examples of gaseous agents are hydrogen, and carbon monoxide. Examples of liquid or solid reducing agents are hydrazine, $NaBH_4$, $NaOCH_3$, (isopropyl)$_3$P, Cu, Na, and Al alkyls, etc. The reduction may be carried out in a separate autoclave or preferably is carried out in the hydrodimerization reactor prior to the introduction of the butadiene. The palladium compound-triorganophosphorus complex may be dissolved in the solvent used in this invention prior to reduction.

The process can be either continuous or batch. The reaction temperature of the process is not critical, however, it is preferred to maintain the reaction between about 0° to about 100° C. preferably between about 20° to about 70° C. The process is conducted under a sufficient pressure to maintain liquid phase conditions at the reaction temperature. Typically the pressure is autogeneous.

The process of this invention is particularly useful when a BBB stream from an oil pyrolysis unit is utilized to provide the butadiene. These BBB streams are the $C_4$ cut from a thermal cracking unit typically containing 30–40% butadiene, 20–35% isobutene and 20–30% n-butenes and many minor components including about ½% of vinylacetylene.

The process of this invention will be further described by the following illustrative embodiments which are provided for illustration and are not to be construed as limiting the invention.

ILLUSTRATIVE EMBODIMENTS

Illustrative Embodiment I

To an 80 milliliter glass-lined autoclave were charged $2.7 \times 10^{-5}$ moles of palladium as a 10% water solution of $Pd(NO_3)_2(OH)_2$, $5.4 \times 10^{-5}$ moles (isopropyl)$_3$ phosphine, 5 ml of pyridine, vinyl acetylene, butadiene and triethylamine formic acid salt ($Et_3N \cdot HOOCH$) in the amount indicated in column 2 in Table I. The stirred reactor was heated to 60° C. for the time indicated in column 2, cooled and the product was analyzed by gas chromatography and mass spectrography. The results are shown in Table I.

Table I

| Test | Reactants | | | Time Hours |
|---|---|---|---|---|
| | Vinyl Acetylene, g | Butadiene, g | $Et_3N \cdot HOOCH$, g | |
| 1 | 0.7 | 0 | 2.52 | 5 |
| 2 | 1.2 | 0 | 1.26 | 1 |
| 3 | 1.2 | 1 | 1.26 | 1 |
| 4 | 0.20 | 1 | 1.26 | 1 |

| Test | Product Analysis | | | |
|---|---|---|---|---|
| | 1-Octen-7-yne, % | 1,7-Octadiene, % | Vinyl acetylene, % | Butadiene, % |
| 1 | 6 | 0.3 | 65 | 27 |
| 2 | 2 | 0 | 96 | 2 |
| 3 | 60 | 0.3 | 22 | 18 |
| 4 | 25 | 65 | 0 | 5 |

Test 1 shows that with a large excess of $Et_3N \cdot HOOCH$ and a long reaction time, some 1-octen-7yne is produced because considerable butadiene is generated from the hydrogenation of vinyl acetylene. No dimer from vinyl acetylene and very little 1,7-octadiene was produced.

Test 2 shows that decreasing the $Et_3N \cdot HOOCH$ and reducing the reaction time has decreased the butadiene and the 1-octen-7-yne. Little reaction was noted and no vinyl acetylene dimer or 1,7-octadiene was produced.

Test 3 with nearly equal amounts of vinyl acetylene and butadiene gave a fairly rapid reaction to 1-octen-7-yne with very little 1,7-octadiene produced. No vinyl acetylene dimer was found.

Test 4 was run with a small amount of vinyl acetylene and excess butadiene. The reaction most probably yields 1-octen-7-yne initially, followed by rapid formation of 1,7-octadiene and the vinyl acetylene is exhausted. Illustrative Embodiment II To an 80 milliliter glass-lined autoclave were charged $2.7 \times 10^{-5}$ moles of the palladium compound listed in Table II, $5.4 \times 10^{-5}$ moles of (isopropyl)$_3$ phosphine, 5 ml of pyridine or 4 ml of dimethylformamide (DMF) solvent, 1 gram of butadiene, vinyl acetylene and formic or its salts in the amount listed in Table II. The stirred reactor was heated to 60° C. for 1 hour, cooled and the product was analyzed by gas chromatography and mass spectrography. The results are shown in Table II.

Table II

| Test | Solvent | Palladium Compound | Vinyl Acetylene, g | Formate Compound, g |
|---|---|---|---|---|
| 5 | DMF | Pd(AcAc)$_2$ | 0.8 | Formic acid, 0.38 |
| 6 | DMF | Pd(AcAc)$_2$ | 0.8 | NH$_4$ Formate, 0.58 |
| 7(a) | DMF | Pd(AcAc)$_2$ | 0.8 | Na Formate, 0.63 |
| 8 | DMF | Pd(AcAc)$_2$ | 0.8 | Na Formate, 0.63 |
| 9(b) | Pyridine | Pd(NO$_3$)$_2$(OH)$_2$ | 1.0 | Et$_3$N . HOOCH, 1.26 |

| Test | Product Analysis | | | |
|---|---|---|---|---|
| | 1-Octen-7-yne, % | 1,7-Octadiene, % | Vinyl Acetylene, % | Butadiene, % |
| 5 | 40 | 0.7 | 10 | 50 |
| 6 | 35 | 0.5 | 12 | 52 |
| 7 | 2 | 0 | 44 | 54 |
| 8 | 10 | 0 | 40 | 50 |
| 9 | 47 | 0.3 | 26 | 27 |

(a)0.5 ml of water added
(b)$5.4 \times 10^{-5}$ moles of (tert-butyl)$_2$POCH$_3$ instead of (isopropyl)$_3$P
(c)2 hours at 75° C.

What is claimed is:

1. The process for preparing 1-octen-7yne which comprises reacting vinyl acetylene and butadiene in the presence of formic acid or a salt of formic acid, optionally a solvent, a catalytic amount of palladium and a tertiary organosphosphorus ligand having the formula:

$$(RO)_a PR_b$$

wherein R is aryl, alkyl, aralkyl or alkaryl with less than about 20 carbon atoms wherein the Rs attached to the phosphorus are the same or different, O is oxygen, a is an integer from 0 to 3 and b is 3-a.

2. The process of claim 1 wherein at least one R of the ligand is benzyl or branched alkyl, aralkyl, alkenyl and cycloalkyl having from 3 to about 10 carbon atoms with branching occurring at a carbon atom no more than two carbon atoms from the phosphorus or oxygen atom.

3. The process of claim 1 or claim 2 wherein the temperature ranges from about 0° C. to about 100° C., the palladium ranges from about $10^{-1}$ to about $10^{-4}$ molar and the ratio of tertiary organophosphorus ligand to palladium is at least 1.

4. The process of claim 1 or claim 2 wherein the solvent is pyridine.

5. The process for preparing 1-octen-7-yne which comprises reacting vinyl acetylene and butadiene in the presence of formic acid or a salt of formic acid, optionally a solvent, a catalytic amount of palladium and a tertiary organo phosphorus ligand having the formula:

$$Z-P(RO)_i R_j$$

wherein Z is a crosslinked synthetic resin, R is aryl, alkyl, aralkyl or alkaryl with less than about 20 carbon atoms wherein the Rs attached to the phosphorus are the same or different, O is oxygen, i is an integer from 0 to 2 and j is 2-i.

6. The process of claim 5 wherein at least one R of the ligand is benzyl or branched alkyl, aralkyl, alkenyl and cycloalkyl having from 3 to about 10 carbon atoms with branching occurring at a carbon atoms no more than two carbon atoms from the phosphorus or oxygen atom.

7. The process of claim 5 or claim 6 wherein the temperature ranges from about 0° C. to about 100° C., the palladium ranges from about $10^{-1}$ to about $10^{-4}$ molar and the ratio of tertiary organosphosphine or phosphinite to palladium is at least 1.

8. The process of claim 5 or claim 6 wherein the solvent is pyridine.

9. The process of claim 5 or claim 6 wherein Z is selected from the group consisting of crosslinked polystyrene, poly(alphaalkyl)acrylate, polycarbonate and polyamide.

* * * * *